United States Patent [19]

Sison

[11] 4,159,303
[45] Jun. 26, 1979

[54] FUME EXHAUST APPARATUS FOR LABORATORY STAINING DISHES

[76] Inventor: Agustin Sison, 1304 Birch St., Union Dale, N.Y. 11553

[21] Appl. No.: 857,104

[22] Filed: Dec. 5, 1977

[51] Int. Cl.² .................... F23J 11/08; G01N 1/28; B01L 1/00
[52] U.S. Cl. .................... 422/104; 98/115 LH
[58] Field of Search ............ 23/292, 259; 98/115 LH

[56] References Cited

U.S. PATENT DOCUMENTS

| 2,715,359 | 8/1955 | Mackintosh et al. | 23/259 X |
| 2,786,740 | 3/1957 | Taylor et al. | 23/259 X |
| 3,713,785 | 1/1973 | Moran | 23/259 X |

Primary Examiner—R. E. Serwin
Attorney, Agent, or Firm—Jacob L. Kollin

[57] ABSTRACT

A fume exhaust apparatus for laboratory staining dishes. The apparatus comprises a housing and an underliner for a staining dish. The underliner and the staining dish with slides therein are displaceable in the housing. An opening is provided in the housing top for extraction of slides. A lifter provided with hooks for removing the slides, one at a time extends through the opening into the staining dish. The lifter is operated by a rack and gear mechanism. A device for moving the underliner and the staining dish thereon, to align consecutive slides with the opening is also provided.

3 Claims, 6 Drawing Figures

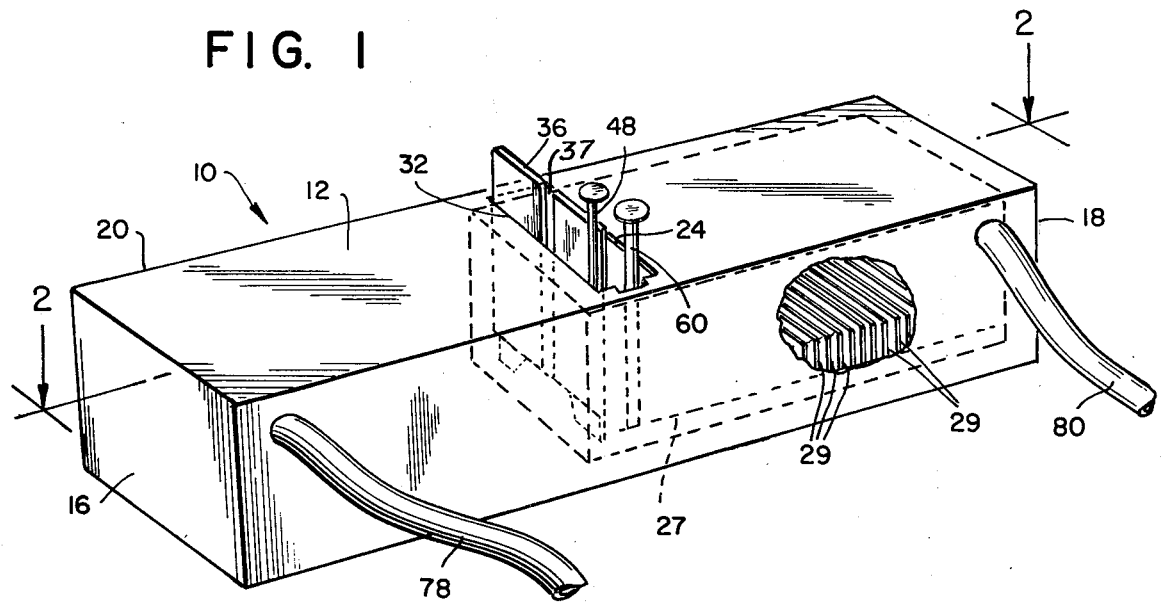
FIG. 1
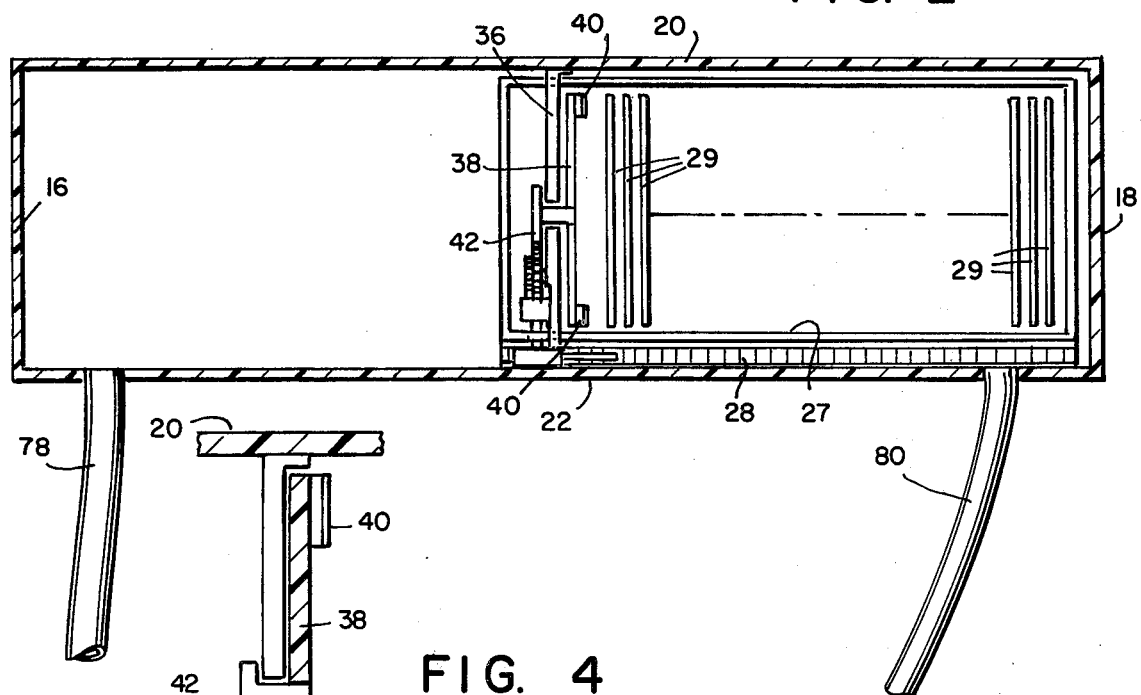
FIG. 2
FIG. 4
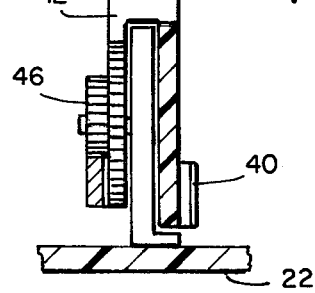

FUME EXHAUST APPARATUS FOR LABORATORY STAINING DISHES

BACKGROUND OF THE INVENTION

The invention relates to a fume exhaust apparatus for use in laboratories in general and in particular for exhausting fumes given off by aromatic spirits known as xylene. Laboratory workers coming in daily contact with xylene, which is used in staining dishes, suffer from headaches, dizziness, malaise, fatigue, shortness of breath, irritability, nausea, burning of the eyes, throat and respiratory "membranes." There have been reports of gastro-intestinal and neurogical disturbances, injury to heart, liver, kidneys and nervous system among such workers. Xylene vapor may cause skin infections and also secondary infections. There have been a number of blood infections, some fatal.

Accordingly, it is the object of the invention to provide a fume exhaust apparatus which will eliminate the above health dangers to the laboratory workers.

Another object of the invention is to provide a device of the above character which will substantially cover the staining dish while permitting the withdrawal of the individual slides.

Another object of the invention is to provide a device of the above character, which is simple and sturdy in construction.

These and other objects of the invention will become apparent from the following description and appended drawing.

In the drawing:

FIG. 1 is a perspective view of the device,

FIG. 2 is a top plan view thereof,

FIG. 4 is a sectional detail taken on line 4 — 4 of FIG. 3,

Figure 3:
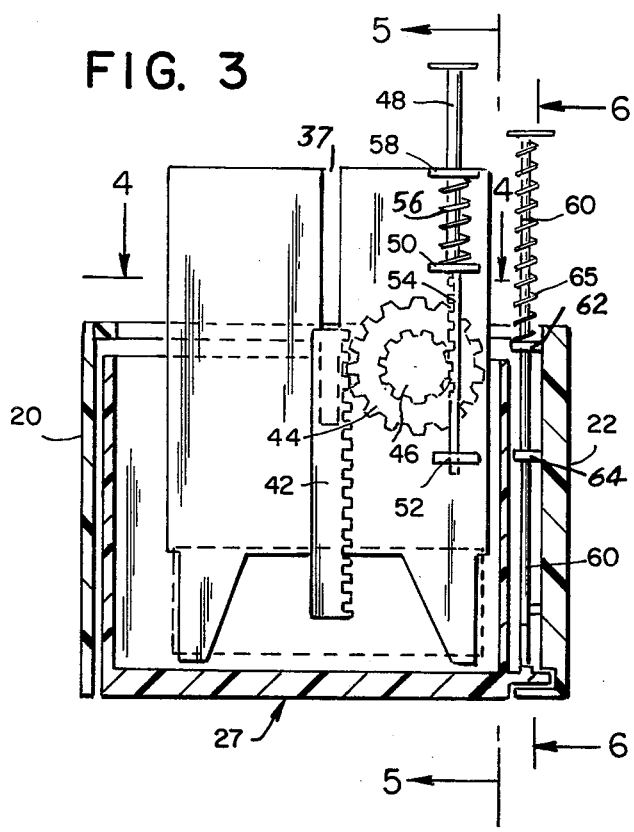
FIG. 3 is a sectional view of the device
Figure 5:
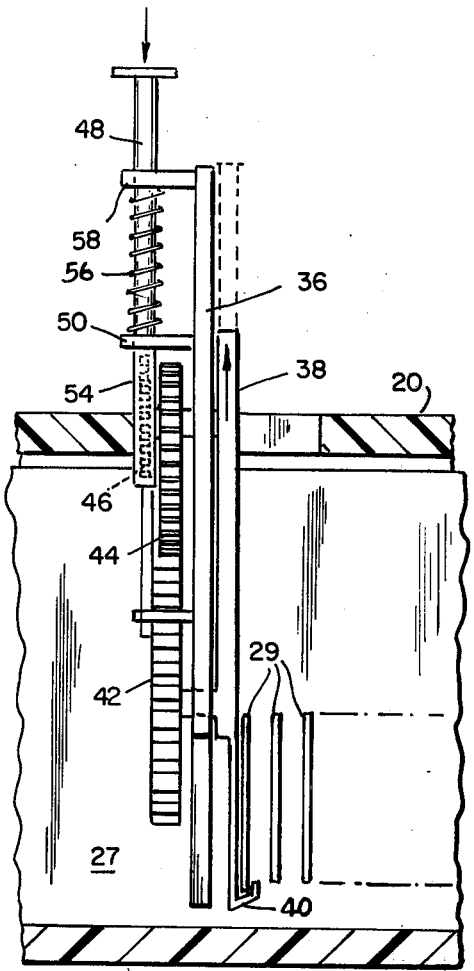
FIG. 5 is a section taken on line 5 — 5 of FIG. 3.
Figure 6:
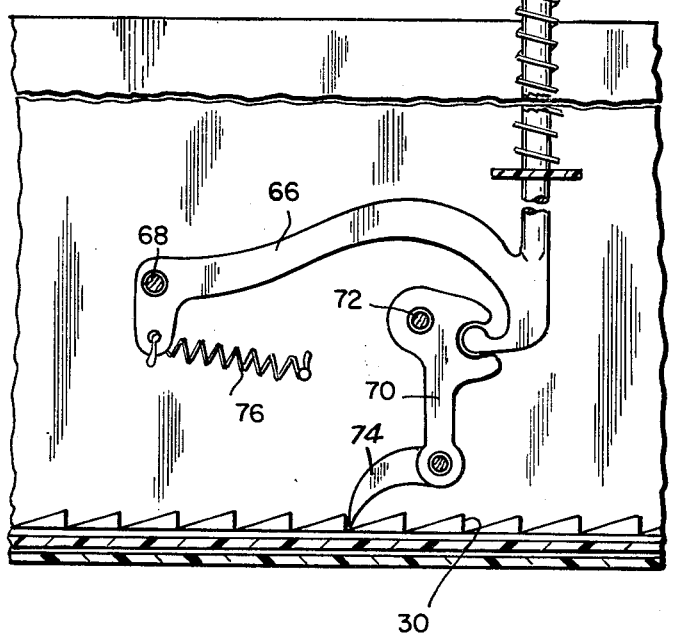
FIG. 6 is a section taken on line 6 — 6 of FIG. 5

Referring now to the drawing in detail, it comprises a housing 10 having a top 12, ends 16, 18 and sides 20, 22. The top of the housing is provided with an opening 24. Secured to the bottom of the housing is an underliner 26 which is provided with a calibrated seale 28 and a toothed portion 30. Positioned movably on the underliner 26 is a staining dish 27 of xylene on which are arranged slides 29. It will be noted that the housing 10 is at least twice the length of the staining dish, to allow it to travel in the housing as will be explained further.

Secured to edge 32 of the slot 24 is a vertically extending plate or "stage" 36 formed with a central slot 37. A lifter 38 is provided for serially lifting the slides for removing these from the staining dish. The lifter with lifting hooks 40 and a rack 42 extending through slot 37.

The rack is in engagement with a larger gear 44 to which is axially secured a smaller gear 46. A rod 48 displacable in guides 50, 52 secured to the stage is provided with teeth 54 which engage with smaller gear 46.

The rod is held in the position shown in FIG. 3 by the bias of spring 56 disposed between guide 52 and flange 58 fixed to the rod. Thus, by depressing rod 48, the rack 42 and lifter 38 are displaced upwardly; through the intermediary of gears 44, 46, at the same time lifting one of the slides above the stage 36, so that it may be grasped and removed by the operator.

To remove the following slides, there is provided a mechanism for displacing underliner 26 bearing the staining dish 27. A plunger 60 displaceable in guides 62, 64 secured to the housing 10 and biased by spring 65 having an arm 66, pivoted to housing 10 at 68 engages with lever 70 also pivoted to the housing at 72. A claw 74 secured to the lever is adapted to engage with the teeth 30. Thus, upon depressing plunger 60 against the bias of spring 76, the claw engages a tooth of the underliner 26 thereby forcing the underliner and the staining dish 27 to move the equivalent of a graduation, thus placing the next following slide above lifter hooks 40, so that it may be removed in the manner described above. The procedure is repeated until all slides have been extracted.

Attached to one of the side walls of the housing, at each end thereof are exhaust hoses 78, 80 which are adapted to be connected to nozzles of a vacuum exhaust system (not shown) usually provided in laboratories.

I claim:

1. Fume exhaust apparatus for laboratory staining dishes, comprising a housing, an underliner displaceable in said housing for supporting a staining dish containing a plurality of parallely disposed slides, said housing having a slotted portion, means in said housing for extracting the slides, means for moving said underliner and a staining dish thereon predetermined distances and flexible tubing communicating with said housing for connection with an exhaust pump.

2. Apparatus as claimed in claim 1, wherein said means for extracting the slides comprises a plate secured in said housing and extending upwardly through said opening, said plate having a central slot extending part way of the plate, a rack slidably mounted in said plate adjacent said slot, a lifter secured to said rack for lifting slides from a staining dish, said lifter being provided with lifting hooks, a pair of gears rotatably mounted on said plate and axially secured to one another, one of said gears being in engagement with said rack, a toothed rod vertically displaceable on guides on said plate and in engagement with the other of said gears and a spring biasing said rod upwardly.

3. Apparatus as claimed in claim 2, wherein the means for displacing said underliner comprises a plunger displaceable in guides secured to an housing wall, said plunger being upwardly biased by a spring, and having an arm engaging with one end of a lever also pivoted to the same said housing wall, a claw pivoted to the other end of said plunger said underliner having a row of teeth for engagement with said claw.

* * * * *